United States Patent [19]

Brattesani

[11] 4,072,694

[45] Feb. 7, 1978

[54] DIOXOLANE DERIVATIVES AND USE AS PHOTOINITIATORS

[75] Inventor: Alan Joseph Brattesani, Los Angeles, Calif.

[73] Assignee: Lee Pharmaceuticals, South El Monte, Calif.

[21] Appl. No.: 613,286

[22] Filed: Sept. 15, 1975

[51] Int. Cl.² ........................................ C07D 317/10
[52] U.S. Cl. .......................... 260/340.9 R; 96/115 P; 260/293.67; 260/332.2 R
[58] Field of Search .................... 260/340.9 R, 340.9

[56] References Cited

U.S. PATENT DOCUMENTS

| | | | |
|---|---|---|---|
| 3,344,148 | 9/1967 | Dietrich et al. | 260/340.9 R |
| 3,944,509 | 3/1976 | Adams | 260/340.9 |

*Primary Examiner*—Ethel G. Love
*Attorney, Agent, or Firm*—Irons and Sears

[57] ABSTRACT

Dioxolane compounds useful to initiate photopolymerization and polymerizable compositions of matter containing such compounds.

11 Claims, No Drawings

DIOXOLANE DERIVATIVES AND USE AS PHOTOINITIATORS

BACKGROUND OF INVENTION

This invention relates to novel dioxolane compounds. More particularly the invention relates to dioxolane compounds useful as photopolymerization initiators and to photopolymerizable compositions of matter containing such compounds.

Polymerization induced by the exposure of monomers to high levels of ultraviolet radiation has been known for many years. The prior art also teaches that the levels of ultraviolet radiation required to initiate polymerization may be reduced by the use of various compounds known as photoinitiators. Such compounds, upon exposure to ultraviolet light of appropriate wave length, provide a source of free radicals which induce polymerization of the monomers present.

Photoinitiators may be generally divided into two categories; namely, those which initiate polymerization when exposed to short wave ultraviolet radiation (less than 280 nm), and those which initiate polymerization only upon exposure to ultraviolet light of longer wave length on the order of 280 to 340 nm.

Photopolymerizable compositions for medical, dental, cosmetic and other applications to the human body must cure effectively upon exposure to long wave ultraviolet radiation because short wave ultraviolet radiation is dangerous to humans. Accordingly, a photoinitiator effective to induce polymerization and hence to induce cure of the composition after the shortest possible exposure to ultraviolet radiation is preferred. In addition, the photoinitiator should be effective at low concentration to preclude objectionable modification of the cured composition. The initiator must also be nontoxic to preclude adverse biological reaction such as dermatological or allergenic irritation or sensitization. Relatively minute concentrations of a biologically unacceptable photoinitiator may cause both irritation and sensization; hence even a low concentration of such a photoinitiator is precluded in photopolymerizable compositions to be applied to the human body.

Low photoinitiator concentration is also preferred in photopolymerizable compositions for industrial applications. Only those photoinitiator molecules near the surface of an applied photopolymerizable composition may react to produce free radicals. The residual photoinitiator molecules act as a diluent in the polymerized composition, migrate to its surface leaving voids which adversely affect its structural properties, and are otherwise objectionable. The problem may be serious when the photoinitiator is present, as it frequently is, in high concentrations up to 30% of the weight of the composition.

It is accordingly one object of this invention to provide novel dioxolane compounds useful, inter alia, as photoinitiators which are effective in relatively low concentration and upon the application of long wavelength ultraviolet radiation. A further object of the invention is to provide novel dioxolane compounds of which at least the embodiments do not irritate or sensitize human tissue. It is a further object of the invention to provide photopolymerizable compositions, including compositions for medical, dental, and cosmetic application, which contain such novel photoinitiators, as well as polymerized or cured, products formed from such compositions.

THE INVENTION

The novel compounds of this invention are dioxolanes having the formula:

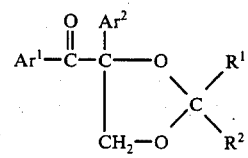
[I]

in which $R^1$ and $R^2$ are H or any organic radical having a molecular weight of 210 or less, preferably below 200, and $Ar^1$ and $Ar^2$ are aromatic radicals selected from the group consisting of unsubstituted phenyl and naphthyl, and non-sterically hindered substituted phenyl or naphthyl radicals in which the substituents each have a molecular weight of 210 or less, preferably below 200, e.g., amino, nitro, chloro-, bromo-, iodo-, fluoro-, lower alkylamino-, anilino-, di- lower alkylamino-, diphenylamino, lower alkoxy, carboxy, hydroxy, sulfonyl, acetyl, propionyl, aldehydro, acetoxy, propionoxy, amido, lower alkylamido, vinyl, lower alkenyl, lower alkynyl, lower alkyl, phenyl, benzyl, naphthyl, cyclohexyl, cyclopentyl, lower alkyl amido, di- lower alkyl amido, phenyl amido, diphenyl amido, and other substituents of less than 200 molecular weight.

Some examples of organic radicals suitable for $R^1$ and $R^2$ include vinyl, hydroperoxy, alkyl or alkenyl groups of up to about 16 carbon atom length, cycloaliphatic groups of lower than 210 molecular weight, phenyl, naphthyl, furyl, piperidyl, thiophenyl, phenoxy, benzoyl, naphthoxyl, phenylcarboxy, various substituted aliphatic groups of up to 200 molecular weight, and other organic radicals within the stated molecular weight limitation.

The preferred embodiments are:

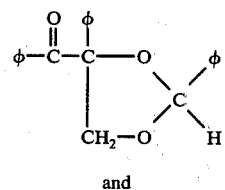
I.

and

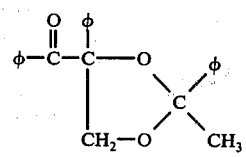
II.

The compounds of the general formula are relatively non-irritating in relation to benzoin derivatives, the usual photoinitiators of commercial use. For instance, the first of the two preferred embodiments was tested against benzoin methyl ether for ability to cause irritation. The material was applied to skin of separate groups of guinea pigs. After repeated applications over a five-day period, using identical concentrations and conditions of application, all the guinea pigs exposed to benzoin methyl ether showed irritation of the skin, whereas some 80% of the guinea pigs exposed to preferred embodiment I showed no irritation and only 20% exhibited some degree of irritation.

EXAMPLES OF PHOTOINITIATOR COMPOUNDS

EXAMPLE I

Preparation of 2,4-diphenyl-4-benzoyl-1,3-dioxolane

α-methylolbenzoin was first prepared by refluxing a slurry of 183 grams benzoin, 84 ml. of 37% aqueous formaldehyde solution, 18 ml. of triethylamine and 250 ml. of denatured ethanol, with magnetic stirring, for 3.5 hours. The reaction mixture was poured into 2.5 l. of water with rapid stirring. The resulting oil was allowed to solidify over a 30-minute period. The solid was filtered and pressed as dry as possible on a Buchner funnel and allowed to drain for 15 minutes.

The crude α-methylolbenzoin thereby obtained was refluxed under a Dean-Stark trap with 0.50 l. benzene to remove about 65 ml. water. 91.2 grams benzaldehyde and 10 grams of p-toluenesulfonic acid were added. An additional 16.5 ml. of water was removed by refluxing for 1.5 hours. The reaction mixture was cooled and saturated with ammonia gas. A salt precipitate and a supernatant yellow benzene solution of the reaction product formed. The precipitated salts were removed by filtration. Benzene was stripped by vacuum from the yellow reaction product solution. The residual oil was distilled at a b.p. of 165°–170° C at 0.02 Torr. to obtain a yield of 255 grams of 2,4-diphenyl-4-benzoyl-1,3-dioxolane which slowly crystallized to a white solid. After recrystallization from hexane, the product melted at 66°–68° C.

This product was subjected to nuclear magnetic resonance ("NMR") and infrared ("IR") analysis.

Nuclear magnetic resonance spectroscopy at 60 MHz showed aryl hydrogen signals at 7.1δ to 8.3δ (15 hydrogens) and within this region phenacyl ortho protons (a multiplet centered at 8.1δ, 2 hydrogens). The methine hydrogen appeared as two singlets at 5.94δ and 6.23δ (1 hydrogen) deshielded by the two ring hydrogens and the adjacent phenyl ring, each geometric isomer accounting for one of the signals. The methylene enantiotopic hydrogens appeared as two sets of paired doublets in the 3.79δ to 5.57δ region (2 hydrogens), one pair of doublets assigned to each isomer. A downfield shift of these protons with respect to the position of methylene protons in a saturated ring was observed and was attributed to the adjacent oxygen and the anisotropic deshielding of the phenyl rings. The coupling constants between these protons corresponded to generally accepted values for geminal hydrogen coupling constant for proton in this environment.

Infrared spectroscopy showed a band at 1680 cm$^{-1}$ confirming the presence of an aromatic ketone and bands in the 1440 cm$^{-1}$ to 1600 cm$^{-1}$ region indicative of phenyl rings.

It was concluded, based on these analyses, that the product was a mixture of geometric isomers of 2,4-diphenyl-4-benzoyl-1,3-dioxolane.

EXAMPLE II

Preparation of 2-methyl-4-phenyl-4-benzoyl-1,3-dioxolane

A solution of 10.0 grams (41 millimoles)αmethylol benzoin, 20.0 grams (45 millimoles) paraldehyde, 0.5 grams p-toluenesulfonic acid and 100 ml. benzene was heated with magnetic stirring to 80°–90° C for 30 minutes under a Dean-Stark trap under conditions such that refluxing occurred, but the vapors condensed before reaching the trap. The temperature of the reaction mixture was then gradually raised to 120°–130° C and 8 ml. water was collected. The reaction mixture was then saturated with ammonia gas, the resulting salt precipitate removed by filtration on a Buchner funnel to provide a benzene solution of the reaction product. The benzene solvent was removed under vacuum. A yield of 11.8 grams of a yellow oil was obtained. The yellow oil was chromatographed on silica gel with 5% ethyl ether in n-hexane elution to provide 9.5 grams of an odorous yellow oil which distilled at 125°–130° C at 20μ vacuum pressure to provide 6.5 grams of a light yellow oil product.

This product was subjected to NMR and IR analysis with the following results:

The 60MHz nuclear magnetic resonance spectrum of this compound showed aryl hydrogen signals at 7.0δ to 8.2δ (10 hydrogens) and within this region phenacyl ortho protons (a multiplet at 8.1δ (2 hydrogens)). The methine hydrogen on the carbon between the two oxygens appeared as two quartets (1 hydrogen) in the 5.00δ to 5.55δ region, each isomer accounting for one of the signals. The three methyl group hydrogens appeared as two doublets at 1.25δ and 1.55δ, each doublet from a different isomer. The two enantiotopic hydrogens appeared as two sets of paired doublets in the 5.45δ to 3.57δ region, one pair of doublets for each isomer.

Infrared spectroscopy showed a band at 1680 cm$^{-1}$ confirming the presence of an aromatic ketone and bands in the 1440 cm$^{-1}$ to 1600 cm$^{-1}$ region indicative of phenyl rings.

The product was concluded, on the basis of examining these spectra, to consist of mixed geometric isomers of 2-methyl-4-phenyl-4-benzoyl-1,3-dioxolane.

EXAMPLE III

Preparation of 4-benzoyl-4-phenyl-1,3-dioxolane

About 273 grams of crude, wet α-methylolbenzoin prepared as described in Example I was refluxed under a Dean-Stark trap with 0.50 liters toluene for about two hours to remove about 50 ml. water. The reaction mixture was allowed to cool and 35 grams paraformaldehyde and 10 grams p-toluenesulfonic acid were added. The reaction mixture was heated for 45 minutes under controlled conditions such that the solvent refluxed below the trap and no water was collected. The temperature of the reaction mixture was then increased and about 16 ml. water was collected over a three-hour period. The mixture was allowed to cool and then saturated with ammonia gas. The resulting salt precipitate was removed by filtration and benzene solvent removed under vacuum from the residual yellow solution containing the solid reaction product. The crude solid reaction product was recrystallized from 1.6 l. of boiling hexane. 156 grams of recrystallized produce having m.p. of 66°–66.5° C was obtained.

This product was subjected to NMR and IR analyses with the following results:

The 60 MHz nuclear magnetic resonance spectrum of this compound showed aryl hydrogen signals at 7.0δ to 8.2δ (10 hydrogens) and within this region phenacyl ortho protons (a multiplet at 8.05δ, 2 hydrogens). The methylene protons on the carbon atom between the oxygens appeared as two singlets at 5.11δ (1 hydrogen) and 5.23δ (1 hydrogen). It is interesting, though not wholly unexpected, that the coupling constant between these two hydrogens was zero, the negligible value being attributed to addition by the two adjacent oxygens of a positive increment to a negative coupling constant, which cancelled one another. The enantiotopic methylene protons were a pair of doublets in the 3.65δ to 5.18δ region (2 hydrogens).

The infrared spectrum of this compound exhibited a band at 1680 cm$^{-1}$ confirming the presence of an aromatic ketone and bands in the 1440 cm$^{-1}$ to 1600 cm$^{-1}$ region indicative of phenyl rings.

The conclusion from these analyses was that the product had the structure of 4-benzoyl-4-phenyl-1,3-dioxolane.

EXAMPLE IV

Preparation of
2,2-dimethyl-4-benzoyl-4-phenyl-1,3-dioxolane

A mixture of 12.1 grams (0.050 mole) of α-methylolbenzoin, 1.0 grams of p-toluene-sulfonic acid, 2.0 grams of anhydrous magnesium sulfate, and 75 ml. of dry acetone was stirred at ambient temperature for 5 days. The mixture was filtered, evaporated, dissolved in benzene, saturated with ammonia gas, again filtered, dried with anhydrous magnesium sulfate, and evaporated. It yielded 11.9 grams (84%) of essentially pure product (m.p. 113°-114°) when recrystallized from benzene.

This product was subjected to NMR and IR analyses. The spectra showed the following:

The 60 MHz nuclear magnetic resonance spectrum of this compound showed aryl hydrogen signals at 7.2δ to 8.2δ (10 hydrogens) and within this region phenacyl ortho protons (a multiplet centered at 8.05δ, 2 hydrogens). The methyl group hydrogens appeared as two singlets at 1.27δ and 1.56δ (6 hydrogens). The methylene enantiotopic hydrogens appeared as a pair of doublets in the 3.79δ to 5.57δ region (2 hydrogens).

Infrared spectroscopy showed a band at 1680 cm$^{-1}$ confirming the presence of an aromatic ketone and bands in the 1440 cm$^{-1}$ to 1600 cm$^{-1}$ region indicative of phenyl rings.

It was accordingly concluded that the structure of the product was that of 2,2-dimethyl-4-benzoyl-4-phenyl-1,3-dioxolane.

EXAMPLE V

Preparation of
2-methyl-2,4-diphenyl-4-benzoyl-1,3-dioxolane

A mixture of 12.1 grams (50 millimoles) of α-methylol benzoin, 6.0 grams (50 millimoles) of acetophenone, 1.0 gram of p-toluenesulfonic acid and 100 ml. of benzene was refluxed under a Dean-Stark trap for 2 hours, the mixture allowed to stand overnight at room temperature, then saturated with ammonia gas and filtered. The resulting oil was distilled at 135°-165° C at 20μ vacuum pressure to yield 10.5 grams of an only partially pure product. 7.2 grams of this product were chromatographed on silica gel with 5% diethyl ether-hexane elution to yield 6.2 grams of a product that was still not entirely pure, which was subjected to NMR and infrared examination as follows:

The 60MHz nuclear magnetic spectrum of this compound showed aryl hydrogen signals at 7.0δ to 8.3δ (15 hydrogens) and within this region phenacyl ortho protons (a multiplet centered at 8.0 (2 hydrogens)). The methyl hydrogens appeared as two singlets at 1.50δ and 1.86δ (3 hydrogens) each geometric isomer accounting for one of the signals. The methylene enantiotopic hydrogens appeared as two sets of paired doublets in the 3.5δ to 5.5δ region (2 hydrogens), one pair of doublets for each isomer.

Infrared spectroscopy showed a band at 1680 cm$^{-1}$ confirming the presence of an aromatic ketone and bands in the 1440 cm$^{-1}$ to 1600 cm$^{-1}$ region indicative of phenyl rings.

It was concluded, based on the NMR and IR spectra that this product contained 2-methyl-2,4-diphenyl-4-benzoyl-1,3-dioxolane in admixture with relatively small quantities (less than 10% by weight) of one or more by-products.

As will be evident to those skilled in the art, products such as 2-phenyl-4-benzoyl-4-naphthyl-1,3-dioxolane, 4-benzoyl-4-naphthyl-1,3-dioxolane, 2-methyl-2-naphthyl-4-benzoyl-1,3-dioxolane, 2,2-dimethyl-4-benzoyl-4-naphthyl-1,3-dioxolane, 2,4-diphenyl-4-naphthoyl-1,3-dioxolane, 4-naphthoyl-4-phenyl-1,3-dioxolane, 2-methyl-2-phenyl-4-naphthoyl-1,3-dioxolane, 2,2-dimethyl-4-naphthoyl-4-phenyl-1,3-dioxolane, 2-phenyl-4-naphthoyl-4-naphthyl-1,3-dioxolane, 2-methyl-4-benzoyl-4-phenyl-1,3-dioxolane, 4-naphthoyl-4-naphthyl-1,3-dioxolane, 2-methyl-2-phenyl-4-naphthoyl-1,3-dioxolane and many others within the scope of the general formula defining the compounds.

EXAMPLES RELATING TO POLYMERIZABLE COMPOSITIONS INCLUDING PHOTOINITIATORS OF THE INVENTION

EXAMPLE VI

A solution of 0.2 parts per hundred by weight of 4-benzoyl-4-phenyl-1,3-dioxolane in a resin mixture of 90 parts by weight of tetrahydrofurfuryl methacrylate and 10 parts of diethylene glycol dimethacrylate was prepared. Five drops of the solution were placed on the bottom surface of an aluminum dish to form a large hemispherical droplet of a nominal thickness of 1.5 mm. Four such droplets were formed near each other on the dish.

The dish was then inserted into an area illuminated with long wave ultraviolet light at an intensity of 8,000μW/cm$^2$, and timing started. A conventional dental examination probe was passed slowly every 5-10 seconds through each droplet in succession until the formation of a film was observed. The time, herein defined as "gel time", was noted. Irradiation and concomitant time observations were continued until the droplets could not be penetrated with the probe. This time, defined herein as "hard set time", was also noted. The procedure was repeated and the time values averaged. Gel time averaged 0.9 minutes and hard-set time averaged 2.9 minutes.

EXAMPLE VII

The above procedure was repeated in all respects except that 2,4-diphenyl-4-benzoyl-1,3-dioxolane was used in place of 4-benzoyl-4-phenyl-1,3-dioxolane. Gel time was 0.9 minutes and hard set time was 2.8 minutes.

EXAMPLE VIII

The above procedure was repeated in all respects using 2-methyl-4-benzoyl-4-phenyl-1,3-dioxolane. Gel time was 0.8 minutes. Hard set time was 3.0 minutes.

I claim:
1. Compounds having the general formula:

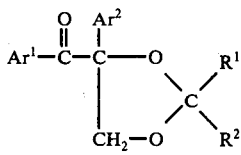

wherein $R^1$ and $R^2$ are each organic radicals selected from the group consisting of vinyl, hydroperoxy, alkyl or alkenyl groups of up to about 16 carbon atom length, cycloaliphatic groups of lower than 210 molecular weight, phenyl, naphthyl, phenoxy, benzoyl, naphthoxyl, phenylcarboxy, and substituted aliphatic groups of up to 200 molecular weight, and $Ar^1$ and $Ar^2$ are each selected from the group consisting of phenyl, naphthyl, non-sterically hindered substituted phenyl, and non-sterically hindered substituted naphthyl in which each substituent is a radical selected from the group consisting of amino, nitro, chloro-, bromo-, iodo-, fluoro-, lower alkylamino-, anilino-, di- lower alkylamino-, diphenylamino, lower alkoxy, carboxy, hydroxy, sulfonyl, acetyl, propionyl, aldehydro, acetoxy, propionoxy, amido, lower alkylamido, vinyl, lower alkenyl, lower alkynyl, lower alkyl, phenyl, benzyl, naphythyl, cyclohexyl, cyclopentyl, lower alkyl amido, di- lower alkyl amido, phenyl amido, and diphenyl amido with the proviso that when $Ar^1$ and $Ar^2$ are phenyl or lower alkyl-substituted phenyl and one of $R^1$ and $R^2$ is lower alkyl, the other may not be lower alkyl, cycloalkyl or phenyl.

2. Compounds according to claim 1 in which $Ar^1$ and $Ar^2$ are each selected from the group consisting of non-sterically hindered substituted phenyl and non-sterically hindered substituted naphthyl.

3. Compounds according to claim 1 in which $R^1$ and $R^2$ are each selected from the group consisting of phenyl and methyl groups.

4. Compounds according to claim 1 in which $Ar^1$ and $Ar^2$ are each phenyl groups.

5. Compounds having the general formula:

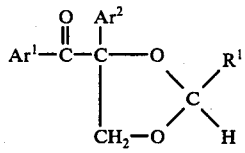

wherein $R^1$ is an organic radical selected from the group consisting of vinyl, hydroperoxy, alkyl or alkenyl groups of up to about 16 carbon atom length, cycloaliphatic groups of lower than 210 molecular weight, phenyl, naphthyl, phenoxy, benzoyl, naphthoxyl, phenylcarboxy, and substituted aliphatic groups of up to 200 molecular weight, and $Ar^1$ and $Ar^2$ are each selected from the group consisting of naphthyl, non-sterically hindered substituted phenyl, and non-sterically hindered substituted naphthyl in which each substituent is a radical selected from the group consisting of amino, nitro, chloro-, bromo-, iodo, fluoro-, lower alkylamino-, anilino-, di- lower alkylamino-, diphenylamino, lower alkoxy, carboxy, hydroxy, sulfonyl, acetyl, propionyl, aldehydro, acetoxy, propionoxy, amido, lower alkylamido, vinyl, lower alkenyl, lower alkynyl, lower alkyl, phenyl, benzyl, naphythyl, cyclohexyl, cyclopentyl, lower alkyl amido, di- lower alkyl amido, phenyl amido, and diphenyl amido with the proviso that $Ar^1$ or $Ar^2$ is not lower alkyl-substituted phenyl.

6. Compounds according to claim 5 in which $Ar^1$ and $Ar^2$ are each selected from the group consisting of non-sterically hindered substituted phenyl and non-sterically hindered substituted naphthyl.

7. Compounds according to claim 5 in which $R^1$ is selected from the group consisting of phenyl and methyl groups.

8. Compounds having the general formula:

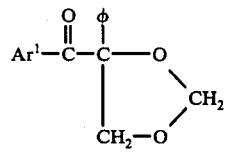

wherein $Ar^1$ is selected from the group consisting of naphthyl, non-sterically hindered substituted phenyl, and non-sterically hindered substituted naphthyl in which each substituent is a radical selected from the group consisting of amino, nitro, chloro-, bromo-, iodo-, fluoro-, lower alkylamino-, anilino-, di- lower alkylamino-, diphenylamino, lower alkoxy, carboxy, hydroxy, sulfonyl, acetyl, propionyl, aldehydro, acetoxy, propionoxy, amido, lower alkylamido, vinyl, lower alkenyl, lower alkynyl, lower alkyl, phenyl, benzyl, naphthyl, cyclohexyl, cyclopentyl, lower alkyl amido, di- lower alkyl amido, phenyl amido, and diphenyl amido with the proviso that $Ar^1$ is not lower alkyl-substituted phenyl.

9. Compounds according to claim 8 in which $Ar^1$ is selected from the group consisting of non-sterically hindered substituted phenyl and non-sterically hindered substituted naphthyl.

10. Compounds having the general formula:

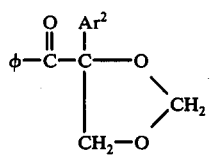

wherein $Ar^2$ is selected from the group consisting of naphthyl, non-sterically hindered substituted phenyl, and non-sterically hindered substituted naphthyl in which each substituent is a radical selected from the group consisting of amino, nitro, chloro-, bromo-, iodo-, fluoro-, lower alkylamino-, anilino-, di- lower alkylamino-, diphenylamino, lower alkoxy, carboxy, hydroxy, sulfonyl, acetyl, propionyl, aldehydro, acetoxy, propionoxy, amido, lower alkylamido, vinyl, lower alkenyl, lower alkynyl, lower alkyl, phenyl, benzyl, naphthyl, cyclohexyl, cyclopentyl, lower alkyl amido, di- lower alkyl amido, phenyl amido, and diphenyl amido with the proviso that $Ar^2$ is not lower alkyl-substituted phenyl.

11. Compounds according to claim 10 in which $Ar^2$ is selected from the group consisting of non-sterically hindered substituted phenyl and non-sterically hindered substituted naphthyl.

* * * * *